(12) United States Patent  (10) Patent No.: US 8,384,895 B2
Albin et al.  (45) Date of Patent: Feb. 26, 2013

(54) SPECTROMETER FLIP TOP SAMPLE HEAD (75) Inventors: Scott Albin, Carlisle, MA (US); Thomas Barraclough, Maynard, MA (US); Michael Morkos, Bellingham, MA (US); Patrick Henning, Concord, MA (US); Eric John Olson, Phillipston, MA (US); Kevin Keough, Canton, MA (US)

(73) Assignee: Spectro, Inc., Chelmsford, MA (US)

( * ) Notice: Subject to any disclaimer, the term of this patent is extended or adjusted under 35 U.S.C. 154(b) by 406 days.

(21) Appl. No.: 12/321,399

(22) Filed: Jan. 20, 2009

(65) Prior Publication Data

US 2010/0182599 A1  Jul. 22, 2010

(51) Int. Cl.
*G01J 3/28* (2006.01)
(52) U.S. Cl. ....................................... 356/326
(58) Field of Classification Search .................. 356/326, 356/244
See application file for complete search history.

(56) References Cited

U.S. PATENT DOCUMENTS

| 5,470,757 | A | 11/1995 | Gagnon et al. |
| 5,764,355 | A | 6/1998 | Gagnon et al. |
| 5,856,870 | A | 1/1999 | Curtiss |
| 6,289,149 | B1 | 9/2001 | Druy et al. |
| 6,322,223 | B1 * | 11/2001 | Smith et al. .................... 359/871 |
| 6,411,434 | B1 * | 6/2002 | Eastman et al. ............... 359/398 |
| 2007/0121113 | A1 * | 5/2007 | Cohen et al. .................. 356/432 |
| 2007/0182961 | A1 | 8/2007 | Chadha et al. |

* cited by examiner

*Primary Examiner* — Tarifur Chowdhury
*Assistant Examiner* — Abdullahi Nur
(74) *Attorney, Agent, or Firm* — Iandiorio Teska & Coleman, LLP (57) ABSTRACT

A spectrometer sample head including a housing, at least one source of radiation in the housing, and a flip top sample cell. First and second hinged plates each include a window aligned with each other when the plate are coupled together. The housing includes a channel for receiving the plates when coupled together for placing the sample in the optical path of the radiation.

24 Claims, 14 Drawing Sheets

SPECTROMETER FLIP TOP SAMPLE HEAD

FIELD OF THE INVENTION

The subject invention relates to spectroscopy and the means to introduce samples for analysis using minimal preparation.

BACKGROUND OF THE INVENTION

Spectroscopic analyzers are used in a variety of applications. For example, infrared analyzers are used to monitor various fluids such as dairy products, fuels, oils, lubricants, in addition to solids, aerosols, gases, and the like.

The primary components of the applicant's infrared analyzer include a source of infrared radiation, typically a filament, which directs infrared radiation through a sample held in a cell. After passing through the sample, the infrared radiation enters an analyzer including a wedge conditioner, a reflective grating, and a detector assembly. The output of the detector assembly is input to a processor programmed with algorithms used to determine the different components of the sample. The results can be depicted on a display linked to the processor.

Absorption of certain infrared frequencies by the sample is indicative of different components in the sample. See U.S. Pat. Nos. 6,289,149; 5,856,870; and U.S. patent application Ser. No. 11/347,482 all incorporated herein by this reference. Additional prior art includes U.S. Pat. Nos. 5,470,757 and 5,764,355 also incorporated herein by this reference.

Various sample heads or cells are known. In one example, a syringe is used to inject a small quantity of oil into a sample cell. Typically, such a cell has ~100 microns thickness. In this case, since the sample cell is filled and not accessible for cleaning, solvent must be introduced in to the cell to remove any remaining sample. The solvent must then be removed from the sample cell which requires forced air. This entire process requires solvent processes to ensure the cell is properly cleaned, and significant time to perform the procedure properly. Moreover, in the field, technicians may not have the skill or time required in order to ensure a proper cleaning process.

BRIEF SUMMARY OF THE INVENTION

It is therefore an object of this invention to provide a novel sample head for a spectrometer which is easier to clean and yet still allows for quantitative analysis by ensuring a predetermined cell thickness.

It is a further object of this invention to provide such a sample head which is easy to use.

It is a further object of this invention to provide such a sample head which is reliable.

It is a further object of this invention to provide such a sample head which is rugged.

The subject invention results from the realization, in part, that a novel, easy to use sample head for a spectrometer includes a flip top sample cell with two hinged plates separable to place a sample on one plate window and, when coupled together, define a sample chamber of a predetermined thickness.

This invention features a spectrometer sample head including a housing, at least one source of infrared radiation in the housing, and a flip top sample cell including first and second hinged plates each including a window aligned with each other when the plates are coupled together. The housing includes a channel for receiving the plates when coupled together for placing a sample in the optical path of the radiation. Typically, the windows are mounted flush in their respective plates.

In one embodiment, there is a seal about one said window. Also, one plate includes a plurality of kinematic mounts (e.g., 3) providing a predefined spacing between the windows, e.g., 100 microns. Alternatively, the kinematic mounts are adjustable. At least one plate may include a magnet set therein for releasably coupling the plates and preferably there are four spaced magnets in the first plate and four spaced magnets in the second plate. The housing channel may include at least one edge groove and at least one plate includes a depending shoe which slides in the edge groove. In the preferred example, the channel includes opposing edge grooves and one said plate includes spaced hinged members each including a shoe. There may be two sources in the housing. The typical sample head further includes a coupler for joining the sample head to a spectrometer.

The subject invention also features a sample cell comprising a housing including a channel therein, a source of radiation in the housing, and a flip top cell received in the channel of the housing. The flip top cell includes first and second hinged plates each with a window aligned with each other when the plates are coupled together. The plates are separable when the flip top sample cell is drawn up out of the channel in the housing to place a sample on one said window.

The subject invention also features a flip top sample cell including first and second hinged plates each including a window, the windows aligned with each other when the plates are coupled together. The plates are separable for placing a sample on one said window.

The subject invention, however, in other embodiments, need not achieve all these objectives and the claims hereof should not be limited to structures or methods capable of achieving these objectives.

BRIEF DESCRIPTION OF THE SEVERAL VIEWS OF THE DRAWINGS

Other objects, features and advantages will occur to those skilled in the art from the following description of a preferred embodiment and the accompanying drawings, in which.

DETAILED DESCRIPTION OF THE INVENTION

Aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings. If only one embodiment is described herein, the claims hereof are not to be limited to that embodiment. Moreover, the claims hereof are not to be read restrictively unless there is clear and convincing evidence manifesting a certain exclusion, restriction, or disclaimer.

Figure 1:
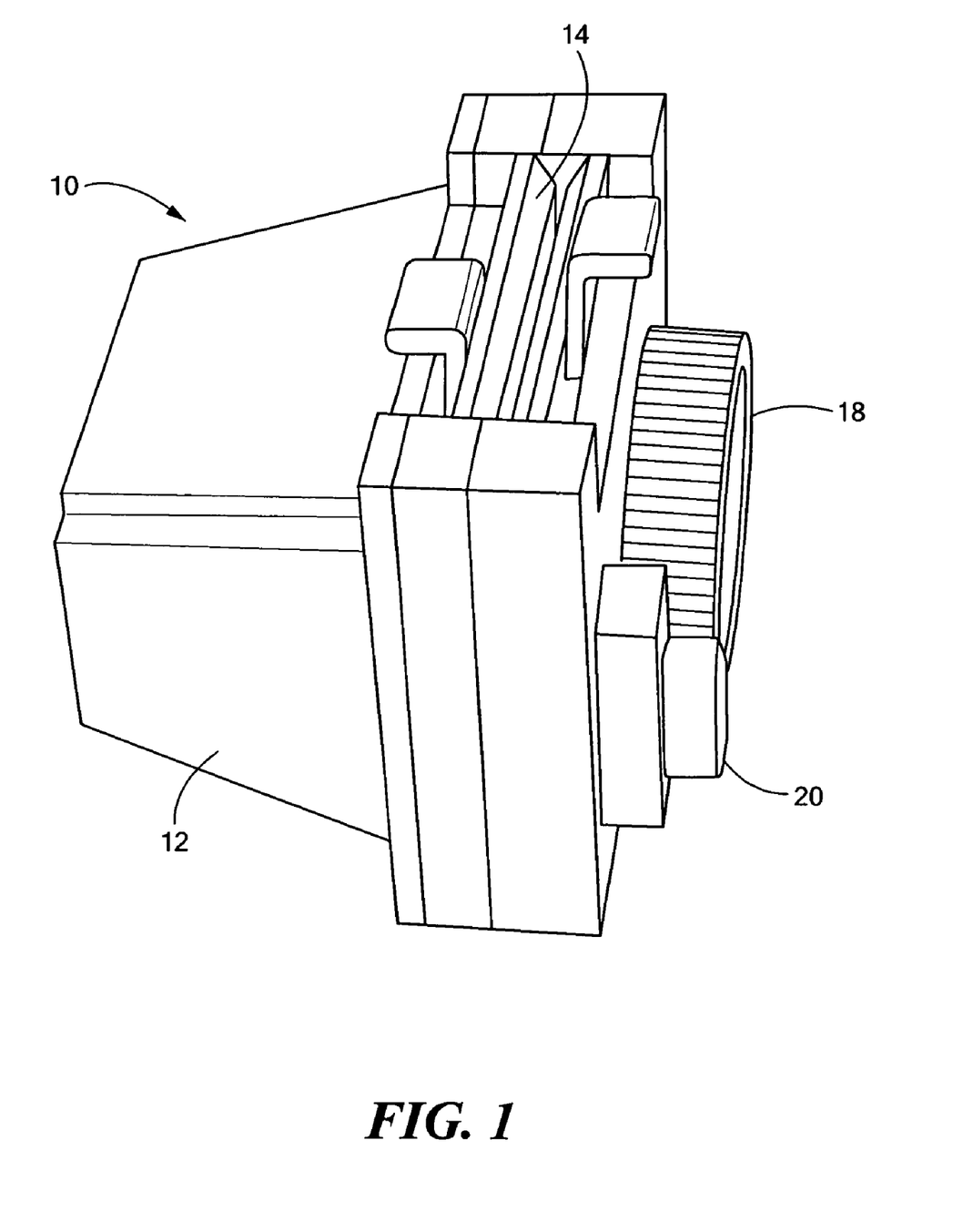
FIG. 1 is a schematic three-dimensional side view of an example of an infrared spectrometer sample head in accordance with the subject invention.
Figure 2:
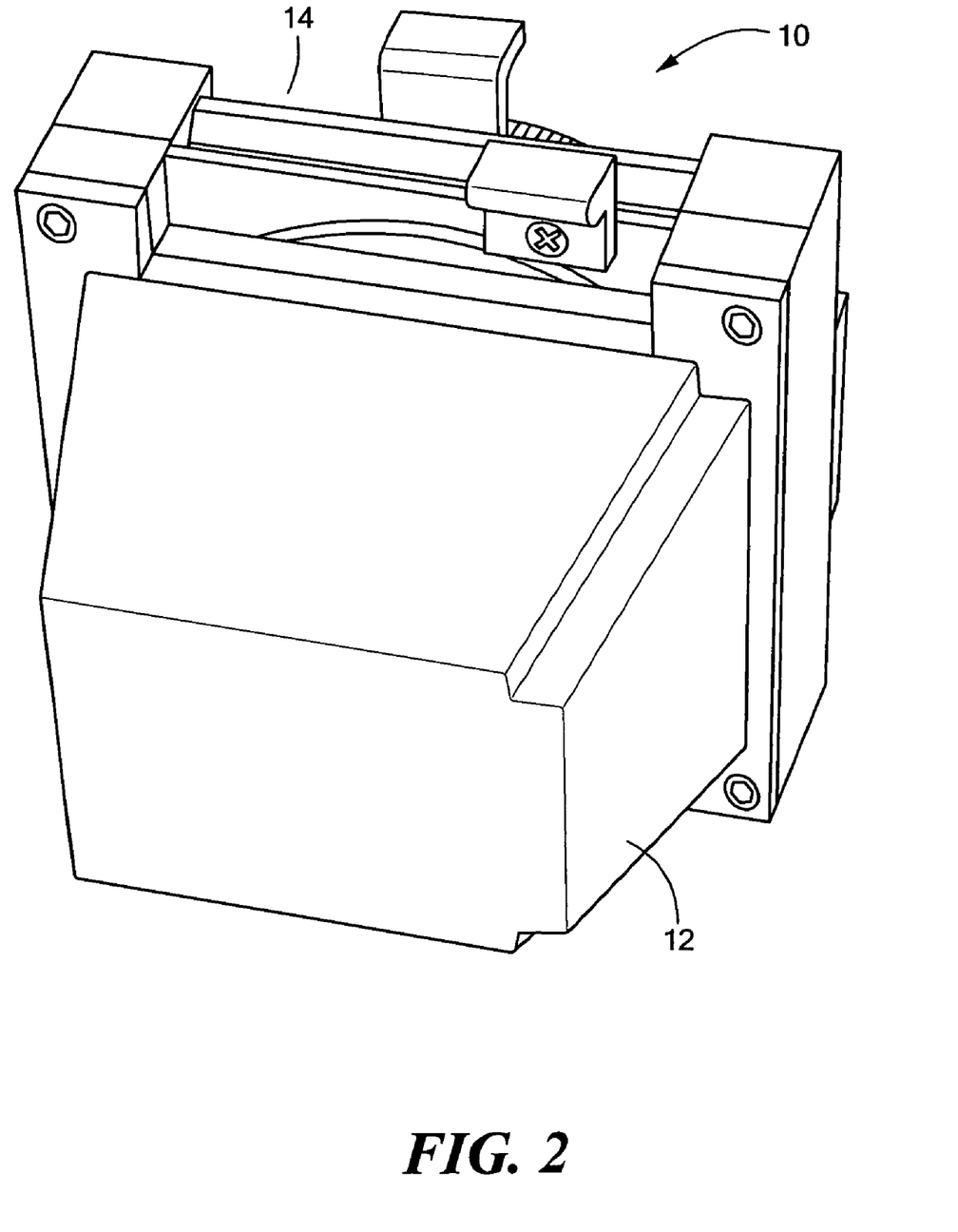
FIG. 2 is a schematic three-dimensional rearward view of the sample head shown in FIG. 1.
Figure 3:
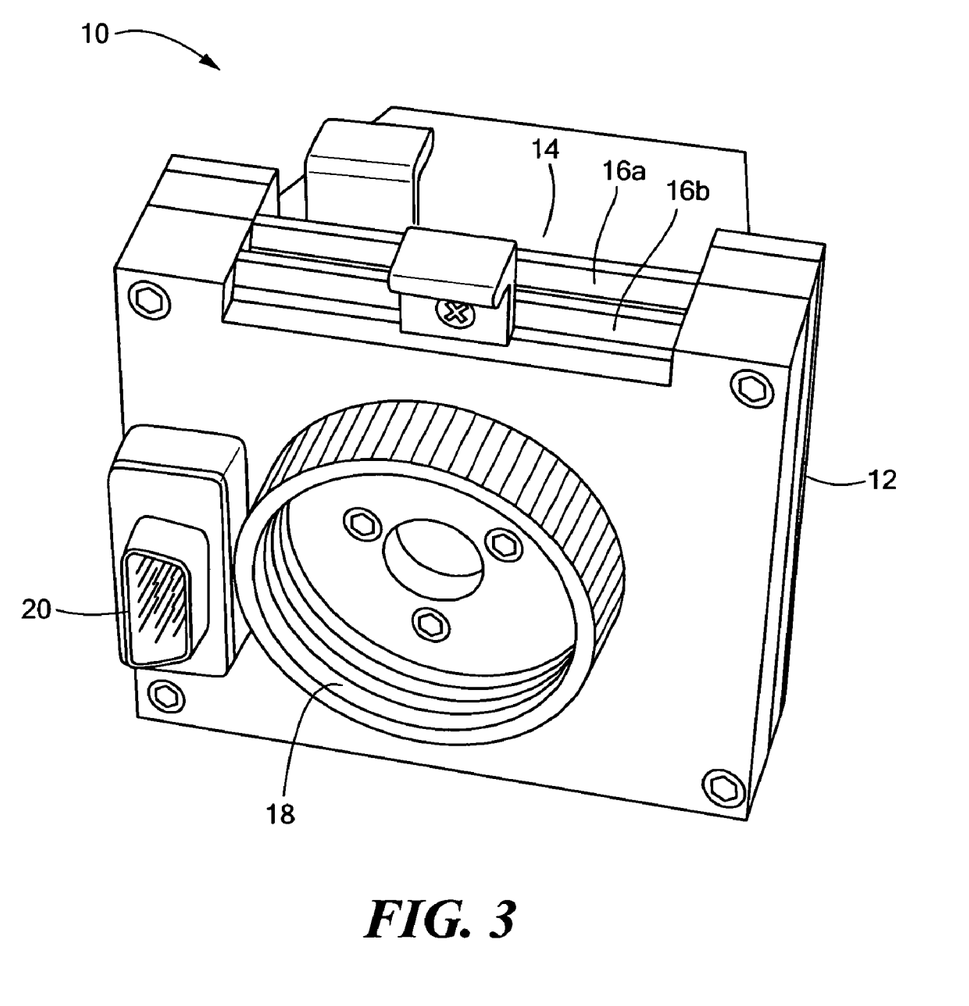
FIG. 3 is a schematic three-dimensional front view of the sample head shown in FIGS. 1 and 2.

FIGS. 1-3 show an example of spectrometer sample head 10 in accordance with the subject invention. Housing 12 includes a source of infrared radiation therein, typically a filament producing radiation in the range of 900 to 4,000 cm$^{-1}$.

Flip top sample cell 14 includes hinged plates 16a and 16b, FIG. 3 shown in position in FIGS. 1-3 within housing 12 and coupled together for spectral analysis. Sample head 10 also includes coupler 18 for joining sample head 10 to a spectral analyzer and electrical connection 20 for energizing and controlling the infrared source within housing 12.

Figure 4:
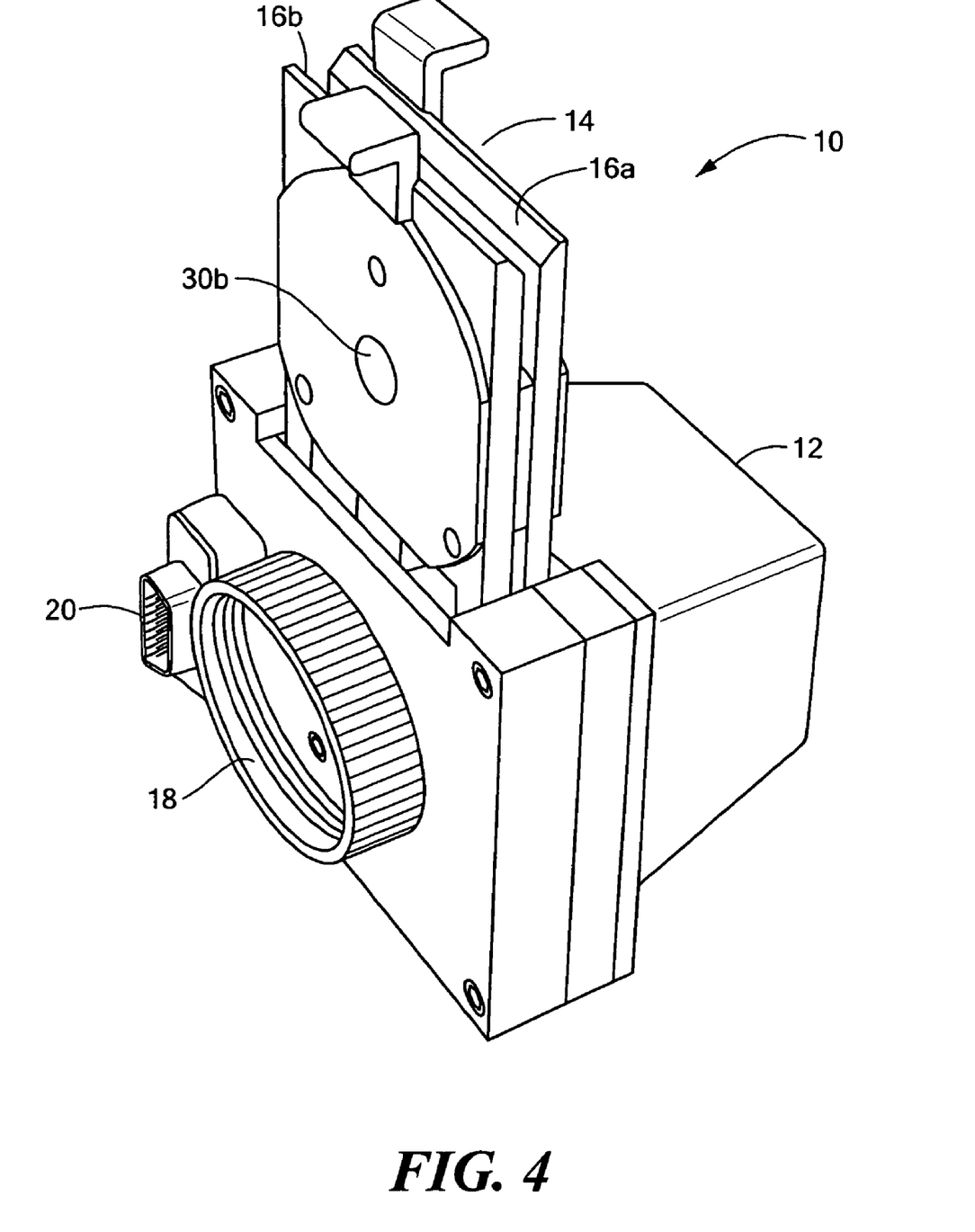
FIG. 4 is a schematic three-dimensional side view showing the sample head of FIGS. 1-3 with the flip top sample cell thereof in its outward position.
Figure 5:
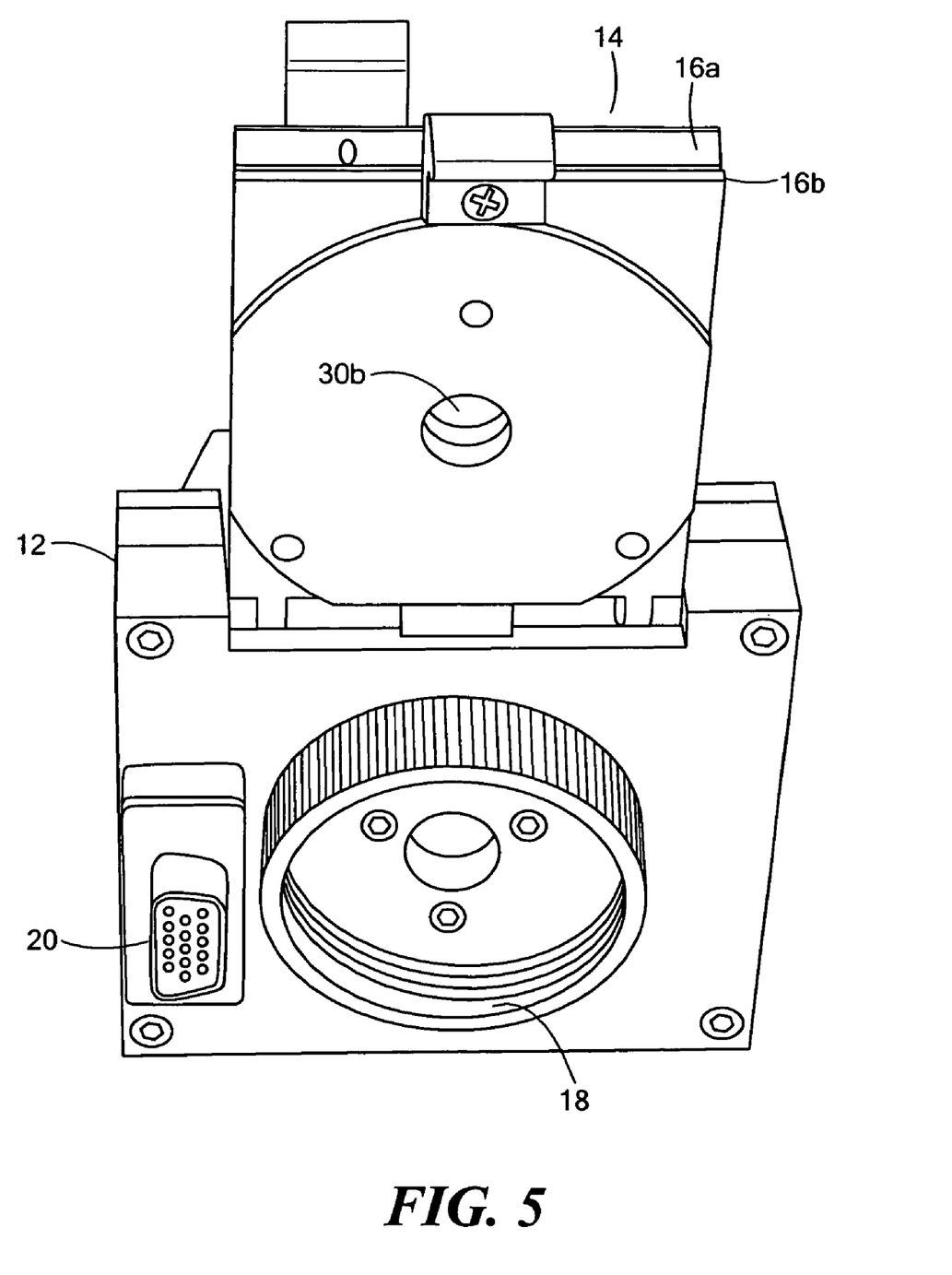
FIG. 5 is a schematic three-dimensional front view of the sample cell shown in FIG. 4.
Figure 6:
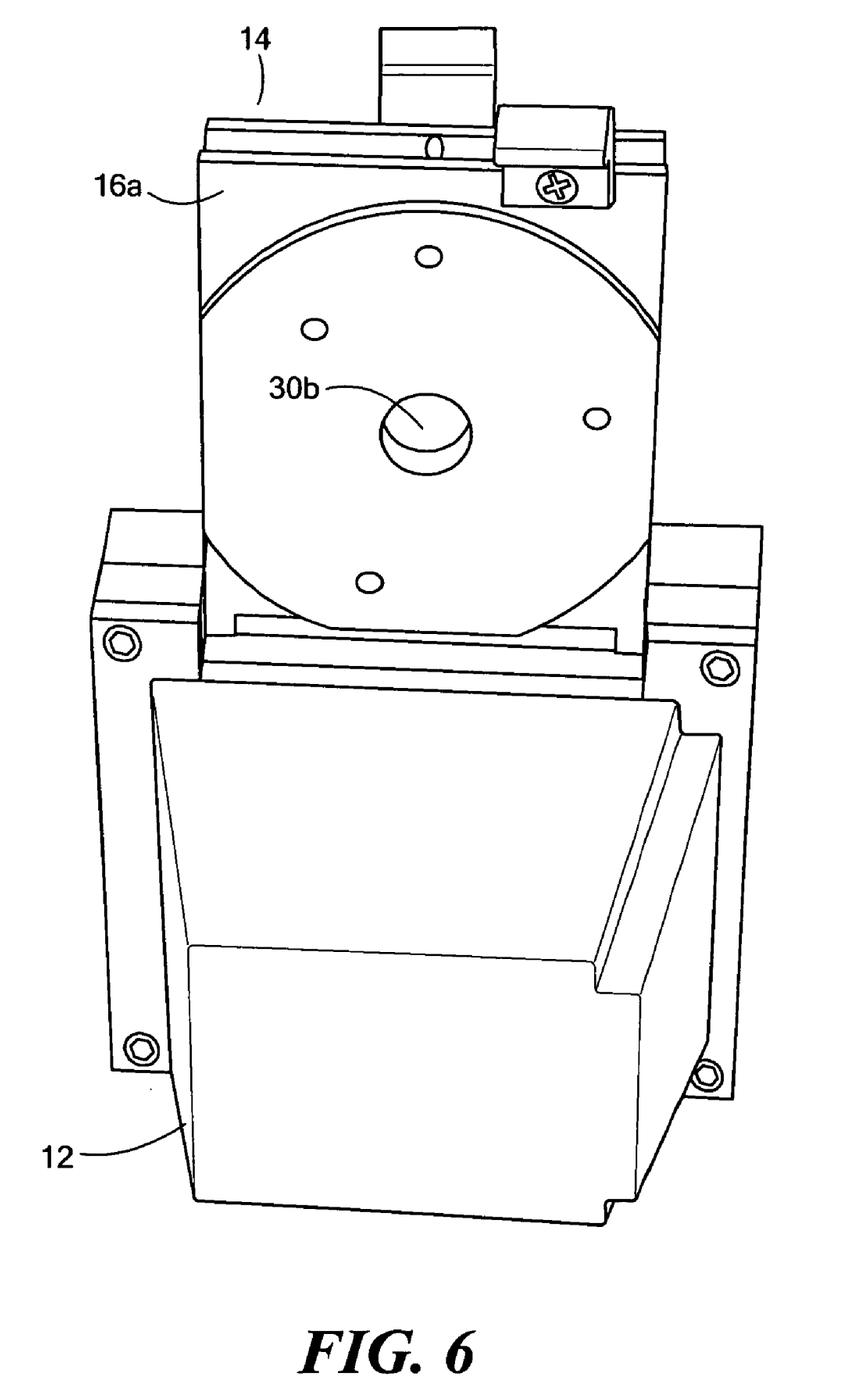
FIG. 6 is a schematic three-dimensional rearward view of the sample cell shown in FIGS. 4-5.

FIGS. 4-6 show flip top sample cell 14 urged upwards out of housing 12 and a window 30a in plate 16a aligned with window 30b in plate 16b. Typical material for windows 30a and 30b is ZnSe and the windows are typically 13 mm in diameter and 2 mm thick.

Figure 7:
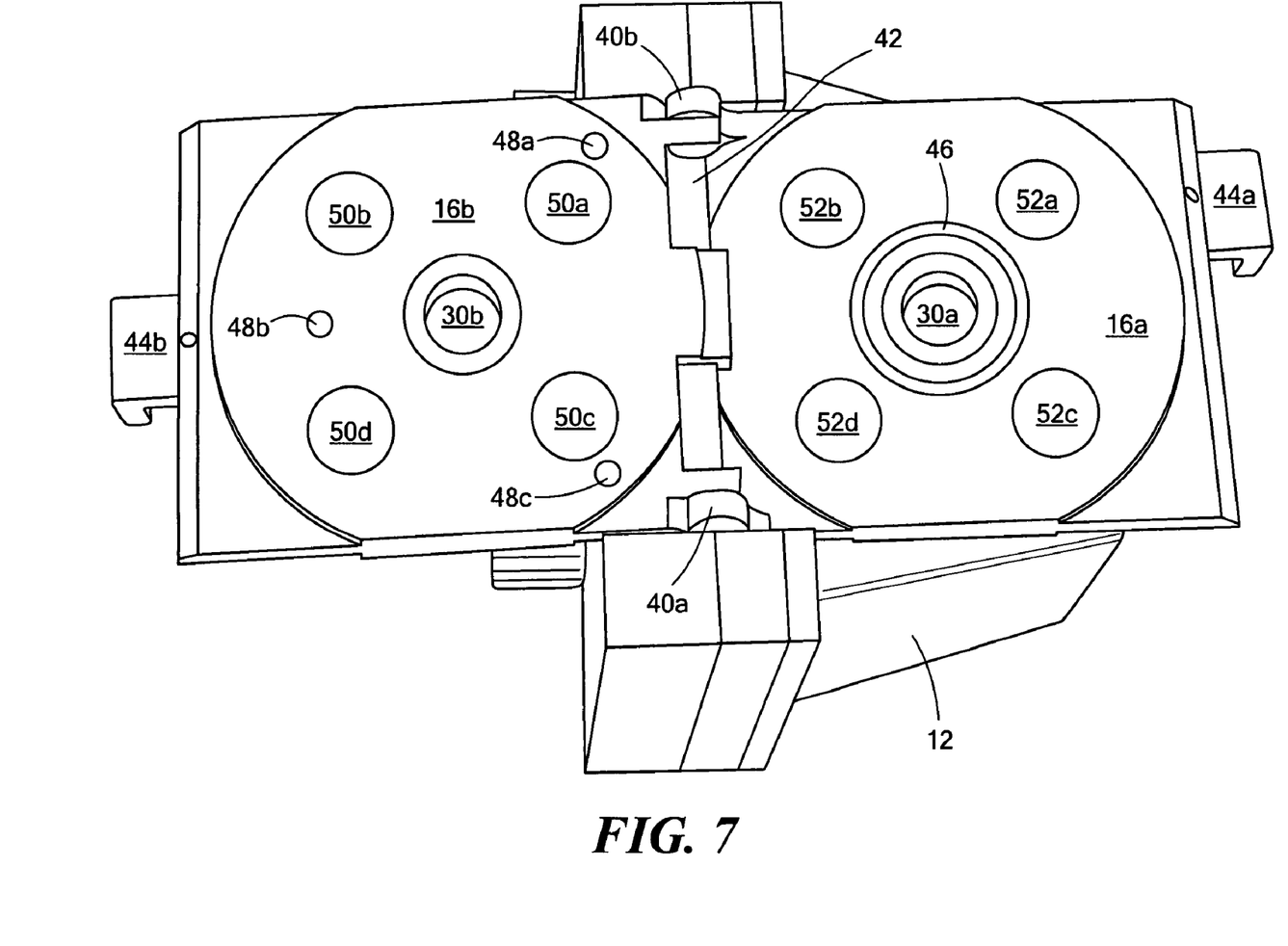
FIG. 7 is a schematic three-dimensional top view showing the flip top sample cell in its decoupled or open configuration.

FIG. 7 shows plates 16a and 16b decoupled and spread apart so that a sample can be placed on window 30a of plate 16a. FIG. 7 also shows more clearly hinges 40a and 40b at the bottom corners of plates 16a and 16b, channel 42 in housing 12 configured to receive plates 16a and 16b when coupled together, and handles 44a and 44b for coupling and decoupling plates 16a and 16b, spreading them apart, urging the coupled plates down in channel 42, and withdrawing them out of channel 42.

In one embodiment, seal 46 (e.g., an O-ring) is disposed about window 30a to ensure that the sample is captured when placed into position for analysis. Kinematic mounts 48a-48c in plate 16b provide a predefined spacing (e.g., 100 microns) between windows 30a and 30b when plates 16a and 16b are coupled together. To keep plates 16a and 16b coupled together once a liquid sample has been placed on window 30a and to maintain the sample thickness desired, plate 16b includes magnets 50a-50d of one polarity and plates 16a includes magnets 52a-52d of the opposite polarity. Plates 16a and 16b are typically made of aluminum and have a surface flatness of L 0.005 inches in the area where they couple together. Windows 30a and 30b are preferably mounted flush with the surface of the plates to (a) prevent any sample from becoming lodged in the sample head and (b) to allow easy removal of sample material using only a wiping action across each plate.

In use, the sample head is fitted to a spectrometer, the flip top cell is urged up and out of housing 12, plates 16a and 16b are decoupled as shown in FIG. 7, and a liquid or solid sample is placed on window 30a. Then, plate 16b is swung over on top of plate 16a whereupon magnets 50a-50d countersunk in plate 16b are attracted to magnets 52a-52d countersunk in plate 16a releasably coupling the two plates together. Kinematic mounts 48a-48c in plate 16b provide a slight separation between plates 16a and 16b and together with the geometry of the plates and windows 30a and 30b define a spacing of 100 microns (or any other desired spacing) between the windows. The coupled together plates are then urged down into channel 42 in housing 12 as shown in FIGS. 1-3 for analysis of the sample.

Figure 8:
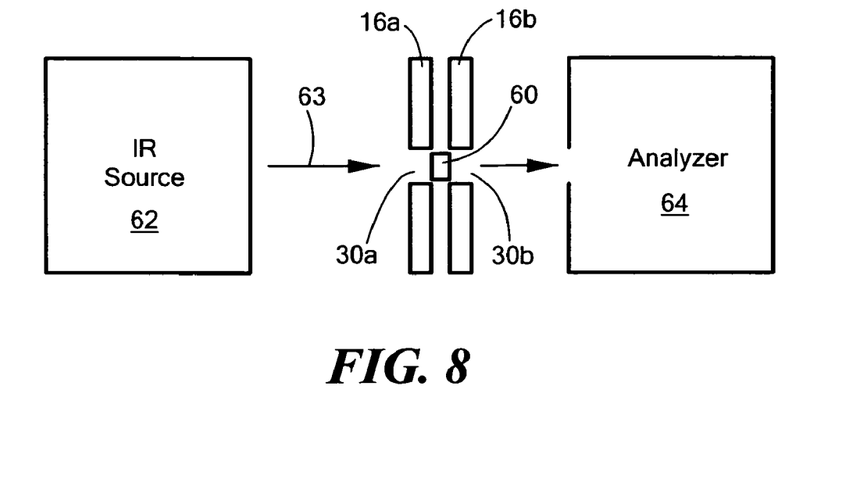
FIG. 8 is a highly schematic block diagram showing the primary components associated with an example of a spectrometer sample head in accordance with the subject invention.

FIG. 8 schematically depicts plates 16a and 16b coupled together and a 100 micron thick sample 60 between windows 30a and 30b. IR source 62 emits radiation 63 which passes through window 30a, sample 60, and window 30b. Thereafter, the radiation proceeds to analyzer 64 which may be engineered in accordance with U.S. Pat. Nos. 6,289,149; 5,856, 870; and/or U.S. patent application Ser. No. 11/347,482. The sample head of the subject invention, however, may be used in connection with other infrared analyzers and even analyzers based on other spectrums of electromagnetic energy, (e.g., visible light, ultraviolet light, and the like).

Figure 9:
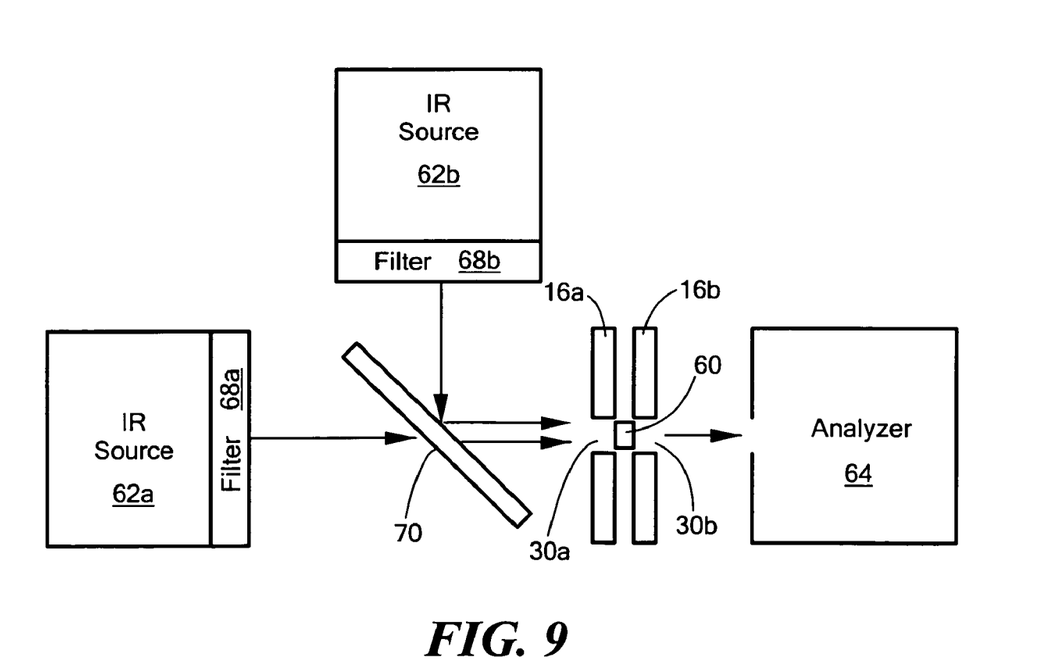
FIG. 9 is another highly schematic block diagram showing the primary components associated with another example of a spectrometer sample head in accordance with the subject invention.

FIG. 9 shows a sample head configuration with two infrared sources 62a and 62b. Each includes a filter 68a, 68b and beam splitter 70 directs infrared radiation from both sources to window 30a in plate 16a. The sources, beamsplitter, and filters are preferably configured such that from each source, a defined and separate infrared frequency band enters the spectrometer. In this way, the bandwidth of the spectrometer can be significantly increased relative to using only one frequency band. The sources are then excited in a fashion such that only one frequency band enters the spectrometer at a given time.

Figure 10:
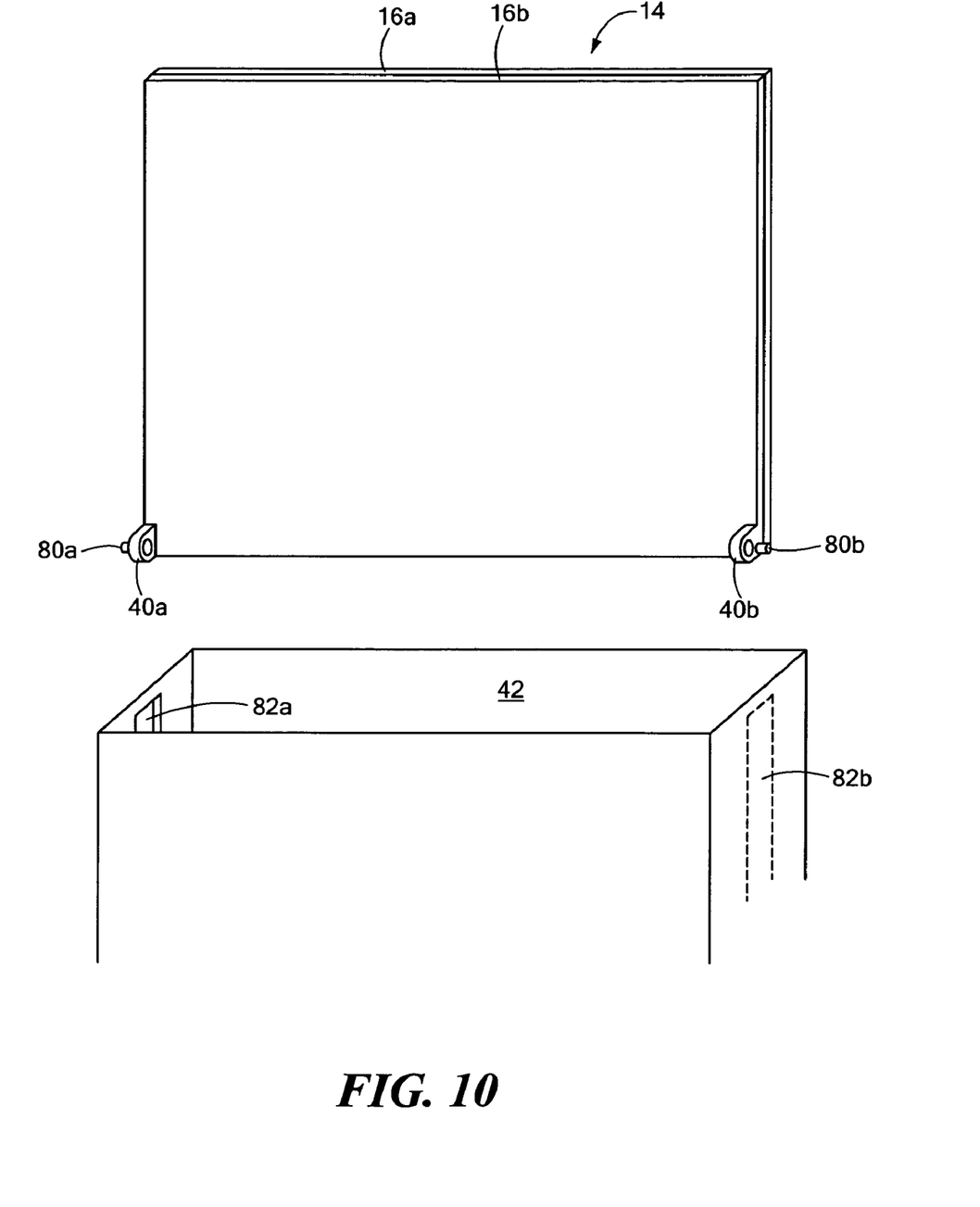
FIG. 10 is a schematic exploded front view showing an example of a sample head channel which receives the flip top sample cell.

Although there are a variety of available designs for the placement of the flip top sample cell within the sample head housing, FIG. 10 shows one configuration where hinges 40b and 40a for plates 16a and 16b each include a depending shoe 80a, 80b sliding in edge grooves or tracks 82a, 82b, respectively, of sample head housing channel 42. The edge grooves 82a, 82b stop short of the top of the channel in this example to prevent the flip top cell from being completely withdrawn out of the sample head housing channel.

Figure 11:
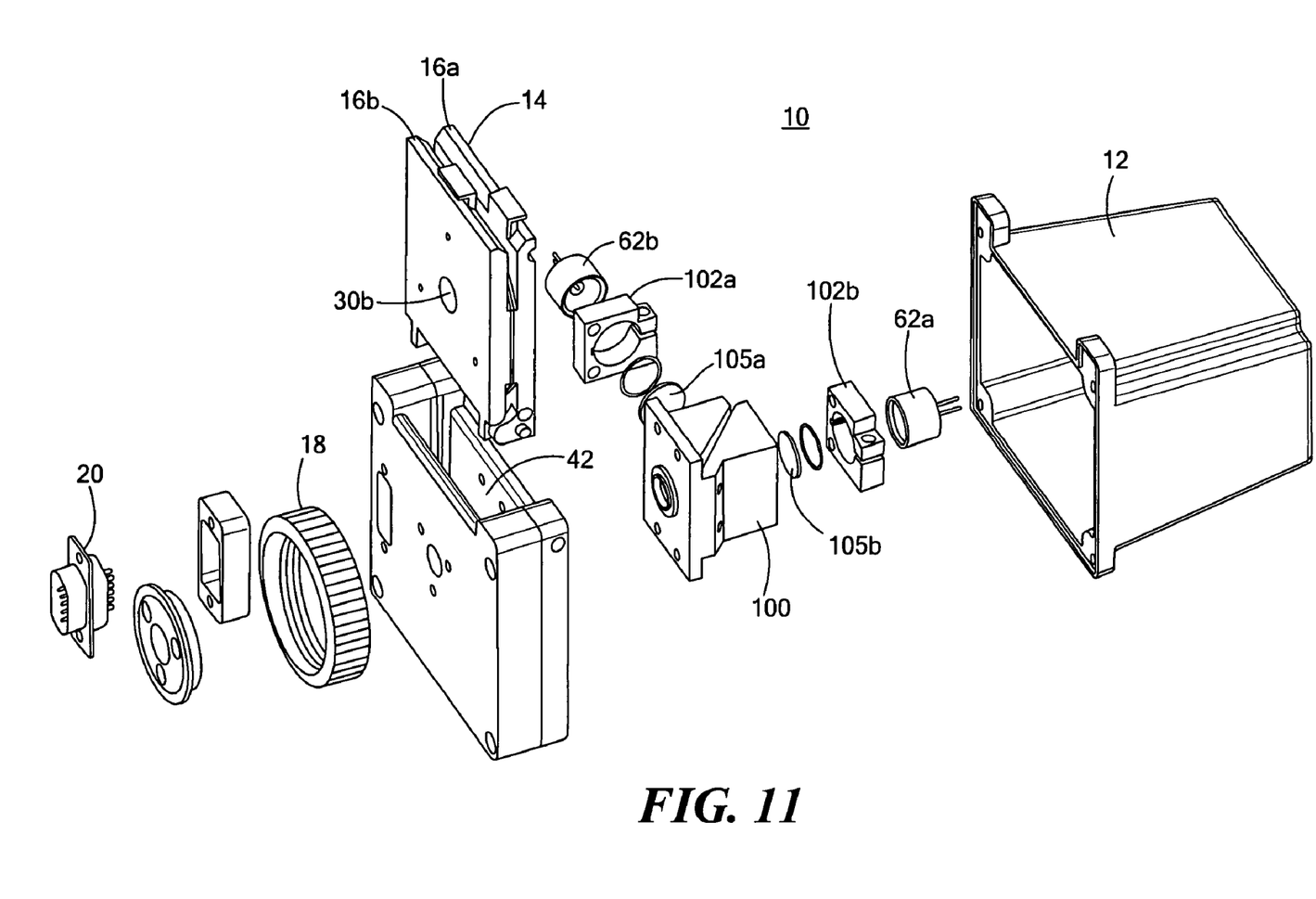
FIG. 11 is an exploded assembly drawing of an example of a sample cell head in accordance with the subject invention.
Figure 12A:
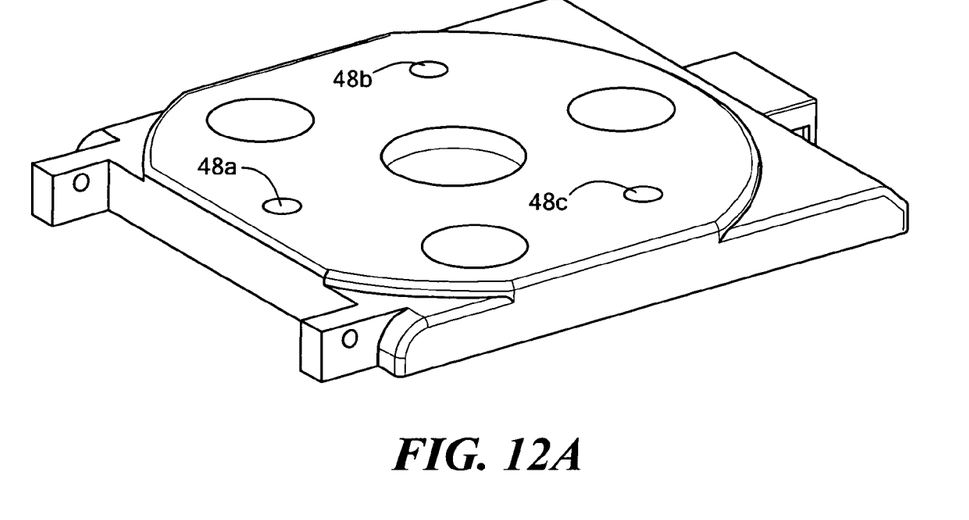
FIGS. 12A and 12B are schematic views of a top plate for the sample cell head of FIG. 11.
Figure 12B:
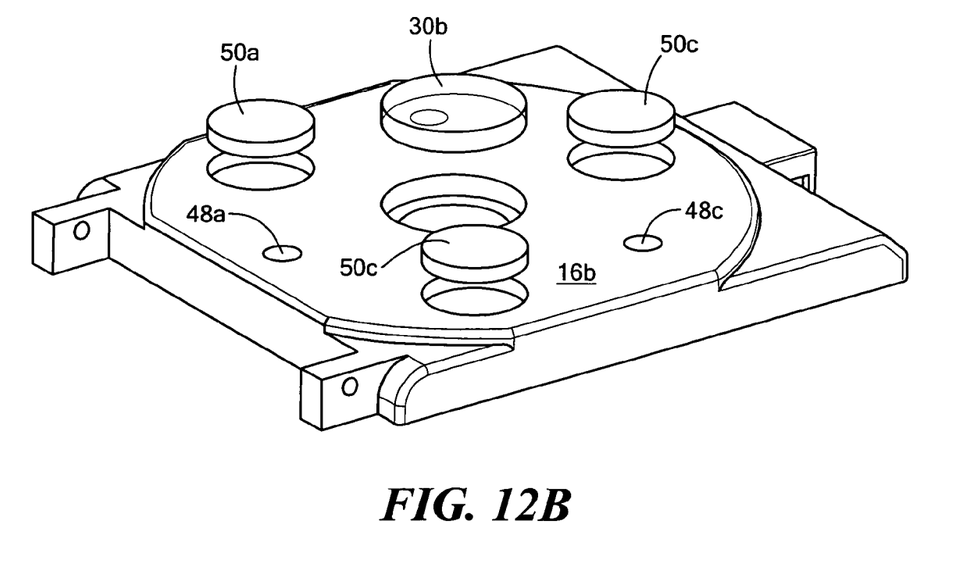
Figure 13:
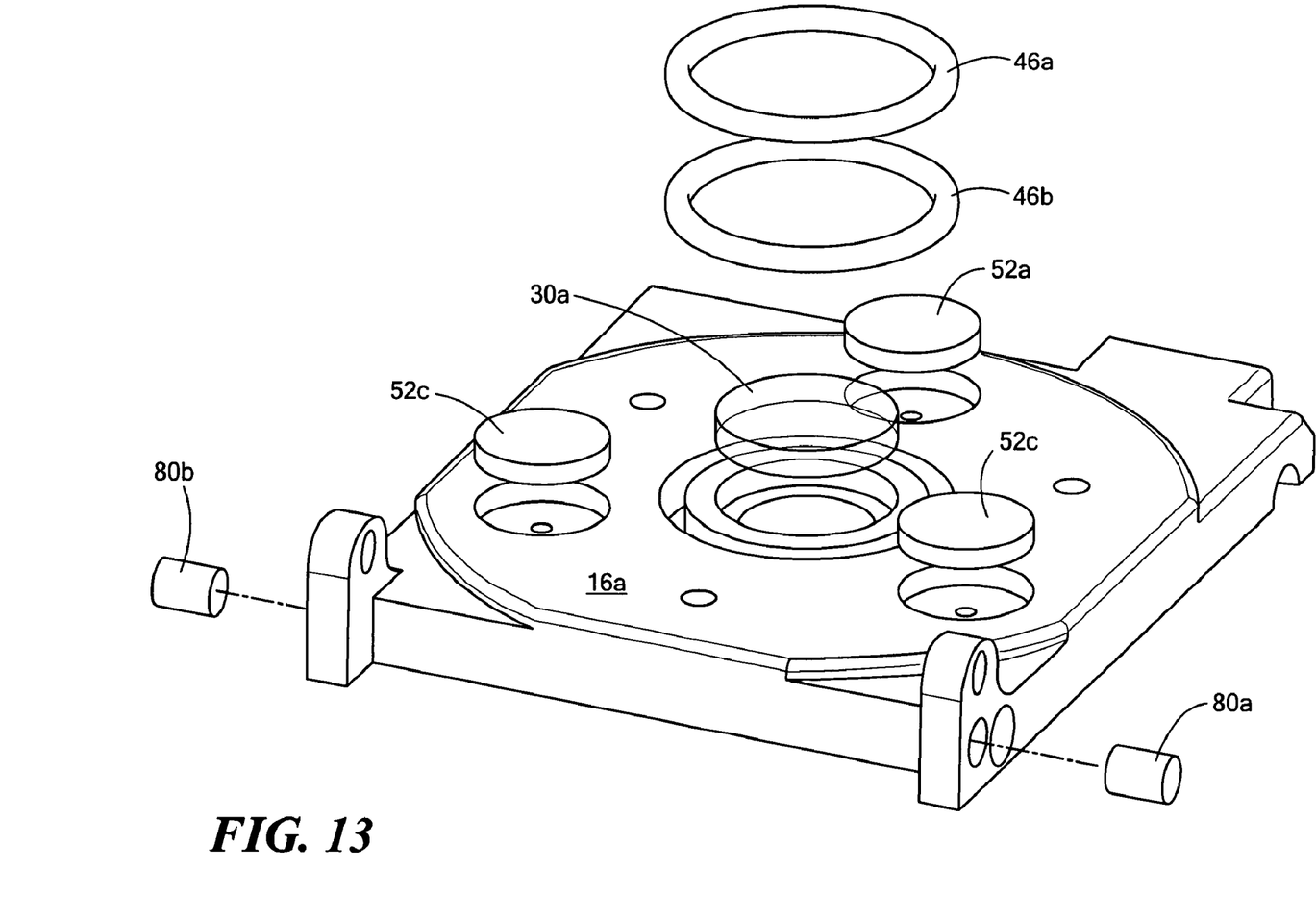
FIG. 13 is a schematic view of the bottom plate for the sample cell head of FIG. 11.

FIGS. 11-13 show an example of a sample cell head in accordance with the subject invention where housing 12 includes the two sources 62a and 62b of radiation held by holder 100 via clamps 102a and 102b also supporting BBP filters 105a and 105b. Channel 42 for flip top sample cell 14 is defined by holder 108.

FIG. 12A shows three steel inserts in top flip top cell plate 16b forming the kinematic mounts and the magnets 50a-50c. FIG. 13 shows two O-ring seals 46a and 46b surrounding window 30a flush within bottom plate 16a. Otherwise, the references correspond to FIGS. 1-7 discussed above.

Figure 14:
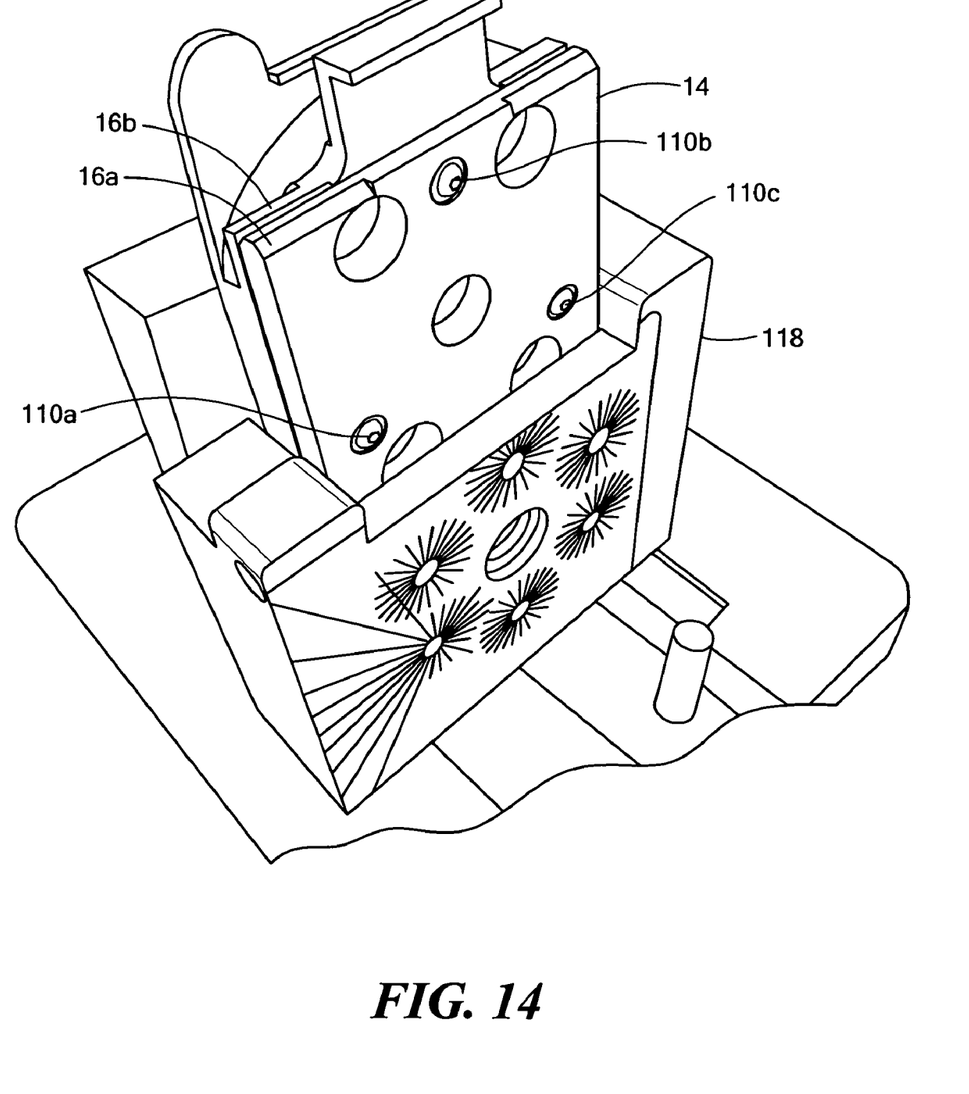
FIG. 14 is a schematic view of an embodiment where the kinematic mounts are adjustable.

In another example, kinematic mounts 48a-48c, FIGS. 7 and 12 are adjustable and O-ring 46, FIGS. 7 and 13, is optional. FIG. 14 shows screws 110a, 110b, and 110c in plate 16a, the distal ends of which can be adjusted relative to plate 16b. By varying the position of screws 110a-110b, the distance between windows 30a and 30b varies. Indeed the distance between plates 16a and 16b can be varied, and so too can the orientation between the plates, e.g., parallel to each other or non-parallel to each other, for calibration.

Figure 15:
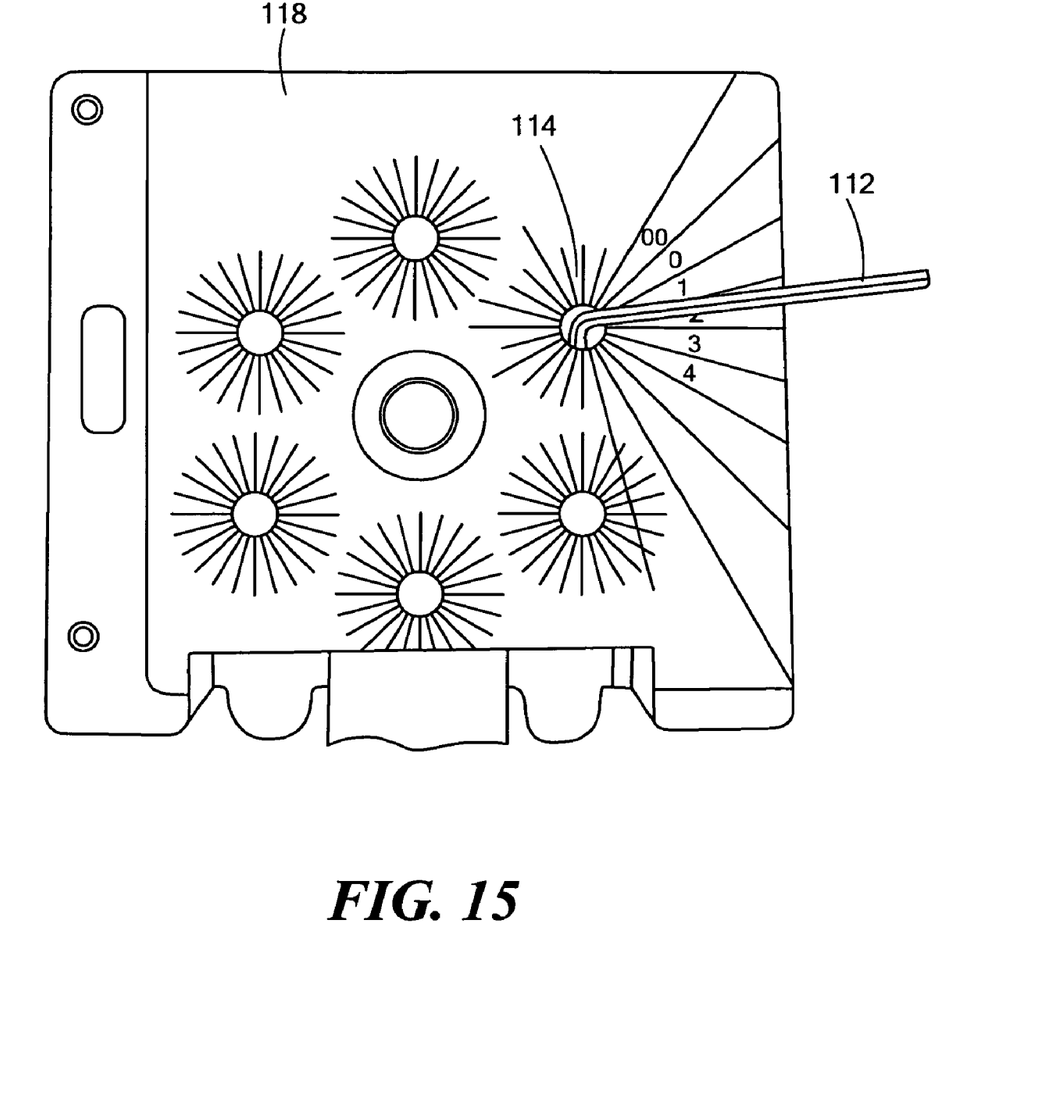
FIG. 15 is a schematic view of a calibrator holder for calibrating the sample cell using interference fringe techniques.

FIG. 15 shows a wrench 112 being used to adjust one kinematic mount screw through an opening 114 in calibration holder 118. One preferred calibration procedure is as follows. First, the windows are cleaned to be free of oil. Next, the three set screws 110a-c are backed out so that when the cell is held up to a light whilst closed, no light is visible through the plates. A Harrick 100 micrometer spacer is placed on the window plate with the three screws and close the cell is closed gently onto the spacer. The screws are tightened clockwise so they are just touching the plate then backed off a ¼ of a turn. An easy way to do this is to place the wrench small side into a screw and then rotate the cell body anticlockwise toward you. As soon as the screw bite onto the apposing surface, the wrench will stop turning and it will need to be backed out a quarter turn. Repeat for the remaining two screws. The cell is then placed into calibration holder 118, FIG. 15 with the screws facing out for interferrometric analysis. Tall fringes should be clearly visible in the interferogram. If they are not visible or are very small check that the set screws are sufficiently backed out, the window is clean and the spacer is seated correctly on the ZnSe window. If the fringes are still small and not clearly defined the spacer should be repositioned in a different position on the window. Place the alien wrench in one set screw so that the long end of the wrench is pointing as close to vertically up as possible (this will depend on the location of the screw and where it was adjusted in the previous step). If the previous step was followed correctly, one should be able to turn the wrench freely a bit in both directions so the wrench falls under its own weight under gravity and it can be supported with a finger. When the screw bites onto the opposing surface, the fringe in the check signal will drop in height and the wrench will remain supported under its own weight. The fringe height should be reduced by 50% so an additional amount of force other than the weight of the wrench may be required. Next move onto the second screw and place the wrench as close to vertical as before and adjust the screw in the same way. When this screw begins to bite, one should see the fringe begin to decrease in intensity. Stop turning the screw until it just begins to disappear into the interferogram. Note if the fringe starts to get taller again when this screw is tightened, back off the screw to its original position and repeat this step with the third screw and the fringe should decrease in height in this scenario. Move onto the third screw place the wrench in vertical position as before so gravity can be used to engage screw into plate. As soon as screw begins to engage, the fringe should begin to reappear and grow again. Turn the screw until about the same size fringe is recorded at the end of the step above. Remove the wrench and take the cell out of the holder, open the cell and remove the spacer. Carefully close the cell and place it back in the holder. Ensure that the fringe is still visible and approximately the same height as before. The fixture now needs to be removed from the sample compartment. Flip the fixture over and place a finger over the cell and apply pressure to the top of the cell to stop it from falling out and also to keep it referenced against the bottom of the cell compartment. Place the wrench so it falls into one of the labeled sectors; 00, 0, 1 or 2 labeled near screw as shown in FIG. 15. The exact location of the wrench will depend on the position that was set previously. When the wrench is located into the screw head, it sits in the middle of sector 2. Turn the wrench clockwise very slowly so it lines up with the line bordering the next sector (in this case sector 3). This is done by holding the fixture up to eye level and we stop turning the wrench as soon as the line at the beginning of the next sector cannot be seen. This sets the starting position for this screw. Note down the sector position of the wrench for reference later. Note if the wrench comes to lie on the border of a sector to begin with it will need to be rotated to the next sector. If the screw lies on the border of sector 2 and 3 then it will need to be removed and placed so it is located before sector 00. Also, it may be easier to rotate the fixture clockwise if the wrench falls into one of the other not so horizontal positions. This makes it easier to line up the wrench with the lines. Remove the wrench from the screw carefully with the cell and holder in the same position. If the cell is flipped over, there is a chance that the wrench will turn which is why we remove it in this position in this step. Place the cell holder back in the sample compartment. The fringe should still be visible in the check signal screen. If the screw was turned a whole sector in the previous step, it may need to be clockwise to bring the fringe back. We now want to adjust the next screw so that we get a minimal fringe height that can still be detected by the calibration program. Turn the screw that made the fringe reappear clockwise to make fringe bigger and anticlockwise to make fringe smaller. Remember you need to have the fringe as small as possible. Once an adjustment is made by either turning the screw clockwise or anticlockwise, the fringe must move from its previous position in the check signal screen, either by whole fringe moving left or right or the fringe height changing. This is important because if it doesn't respond to a screw turn then the screw is no longer in contact with the opposing surface. It is important to make the fringe as small as possible as this will have benefits later in the procedure. Take a clean cell background and measure the path length. If an error appears and the cell path length is not computed then the fringe is not tall enough and you will need to go back and apply further clockwise rotation on the screw to make the fringe taller. If the cell path length is computed without any problems, note the number calculated in micrometers. Note it is often best to start with a very small fringe that fails then with minor adjustments make the fringe taller so it passes. As has previously been mentioned this will reap benefits later in the procedure when we evaluate the degree of fringing based on the wedge. Remove the holder and turn it upside down whilst holding the cell in place. Place the wrench carefully into the position noted before. One should still not be able to see any of the sector line. Carefully turn the wrench a further six sectors (90° from start position) and line up the edge of the wrench with the final sector line as before and stop turning the wrench when the line can no longer be seen. By turning the wrench 90°, an additional 16 micrometers of path length is induced into the cell and an optical wedge is produced which will totally eliminate the effects of fringing. Very carefully remove the wrench from the set screw as before with the holder upside down as before. Place the cell holder back into the sample compartment and view the interferogram. One should not see any evidence of a fringe. As a further more important check, view the power spectrum and zoom in the area to the left of the $Co_2$ absorbance band. One should notice minimal fringing noise in the region of the power spectrum. If too much noise does still exist, go back a few steps and reset fringe correction and try to minimize the fringe height. Next, place two drops of 5606 hydraulic fluid onto the window with the screws using a plastic pipette. Very gently and carefully close the cell making sure not to induce any air bubbles. Place the cell in the holder with the screws facing to the right. After the analysis is completed, record the results.

Interference fringes have traditionally been used to very accurately derive parallel cell path length. In a parallel cell, the distance from the interfering secondary centerburst (fringe) to the centerburst is equal to the path length of the cell. The distance between interferogram points can be accurately derived knowing the wavelength of the monochromatic reference laser. This theory is used to derive the parallel path length and also the wedged path length in this procedure. The wedged distance is derived by calibrating the angular rotation of the fine pitch screws into micrometers. When a single screw is rotated into the apposing plate the two surfaces move apart and a wedge is formed between the plates pivoting on the other two screws. The difference in the fringe location is equal to the change in path length caused by the rotation of a screw-calibration of a 15 degree turn for three different screw locations resulted in an average 2.7 micrometer change in actual path length. It's not possible to measure the travel of a fringe for 90° of rotation which is required to sufficiently remove fringing because the fringe disappears. So, instead we can just sum six, ¼ turns equating to 16.2 micrometers in path length change.

We can also prove that this additional wedged dimension is correct by using an optical microscope to derive the distance that a ¼ turn of a screw equate to. Using this distance and the geometry of the cell enables the wedged distance to be easily calculated using basic trigonometry. The surface features of the flat head of the screw are focused in on using a ×1000 magnification lens using a calibrated 1 micrometer focus wheel. The difference in the position of the focus wheel (in micrometers) when the screw is turned out a further ¼ turn and re-focused is equal to the distance traveled by the screw. Calibration of the travel of the screw with a ¼ turn using this method resulted in a consistent distance of 49 micrometers using different ¼ turns on the cell holder. A ¼ turn of one fine pitch screw also produces an additional 16.3 micrometers of wedged path length on top of the original parallel path length.

The result, in any embodiment, is a sample head for a spectrometer which automatically ensures a predefined sample thickness. The sample head of the subject invention is also easy to use, reliable, and rugged.

Thus, although specific features of the invention are shown in some drawings and not in others, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments.

In addition, any amendment presented during the prosecution of the patent application for this patent is not a disclaimer of any claim element presented in the application as filed: those skilled in the art cannot reasonably be expected to draft a claim that would literally encompass all possible equivalents, many equivalents will be unforeseeable at the time of the amendment and are beyond a fair interpretation of what is to be surrendered (if anything), the rationale underlying the amendment may bear no more than a tangential relation to many equivalents, and/or there are many other reasons the applicant can not be expected to describe certain insubstantial substitutes for any claim element amended.

Finally, other embodiments will occur to those skilled in the art and are within the following claims.

What is claimed is:

1. A spectrometer sample head comprising:
    a housing;
    at least one source of radiation in the housing; and
    a flip top sample cell including first and second hinged plates;
    a window through the first plate with a pane in said window;
    a window through the second plate with a pane in said window;
    the windows aligned with each other when the plates are coupled together, one said pane for receiving a sample thereon,
    the housing including a channel for receiving the plates when coupled together for placing a sample in the optical path of the radiation.

2. The sample head of claim 1 further including a seal about one said window.

3. The sample head of claim 1 in which one said plate includes a plurality of kinematic mounts providing a predefined spacing between the windows.

4. The sample head of claim 3 in which the predetermined spacing is 100 microns.

5. The sample head of claim 3 in which said kinematic mounts are adjustable.

6. The sample head of claim 3 in which there are three kinematic mounts.

7. The sample head of claim 1 in which at least one plate includes a magnet set therein for releasably coupling the plates.

8. The sample head of claim 7 in which there are four spaced magnets in the first plate and four spaced magnets in the second plate.

9. The sample head of claim 1 in which the channel includes at least one edge groove and at least one plate includes a depending shoe which slides in the edge groove.

10. The sample head of claim 9 in which the channel includes opposing edge grooves and one said plate includes spaced hinged members each including a shoe.

11. The sample head of claim 1 in which there are two sources in the housing.

12. The sample head of claim 1 further including a coupler for joining the sample head to a spectrometer.

13. The sample head of claim 1 in which each window is mounted flush within its respective plate.

14. A sample cell comprising:
    a housing including a channel therein;
    a source of radiation in the housing; and
    a flip top cell received in the channel of the housing, the flip top cell including first and second hinged plates;
    a window through the first plate with a pane therein;
    a window in the second plate with a pane therein;
    the windows aligned with each other when the plates are coupled together,
    the plates separable when the flip top sample cell is drawn up out of the channel in the housing to place a sample on one said window.

15. The sample cell of claim 14 further including kinematic mounts setting the spacing between said windows.

16. The sample cell of claim 15 in which said kinematic mounts are adjustable.

17. A flip top sample cell comprising:
    first and second hinged plates;
    a window through the first plate with a pane therein;
    a window in the second plate with a pane therein;
    the windows aligned with each other when the plates are coupled together; and
    the plates separable for placing a sample on one said pane.

18. The sample cell of claim 17 in which the windows are mounted flush within the respective plates.

19. The sample head of claim 17 further including a seal about one said window.

20. The sample head of claim 17 in which one said plate includes a plurality of kinematic mounts for providing a predefined spacing between the windows.

21. The sample head of claim 20 in which the kinematic mounts are adjustable.

22. The sample head of claim 20 in which there are three kinematic mounts.

23. The sample head of claim 17 in which at least one plate includes a magnet set therein for releasably coupling the plates.

24. A flip top sample cell comprising:

a first plate including a first window therethrough with a pane therein;

a second plate hinged to the first plate and including a window therethrough with a pane therein;

the windows aligned with each other when the plates are coupled together;

the plates separable for placing a sample on one said pane;

at least one said plate including a plurality of kinematic mounts for providing a predefined space in between the windows; and at least one plate including a magnet set therein for releasably coupling the first and second hinged plates together.

* * * * *